US009869638B2

(12) United States Patent
Jiang et al.

(10) Patent No.: US 9,869,638 B2
(45) Date of Patent: Jan. 16, 2018

(54) METHOD FOR DETECTING TIME-RESOLVED FLUORESCENCE BASED ON PRINCIPLE OF PHASE BALANCED FREQUENCY MULTIPLICATION MODULATION

(71) Applicant: Suzhou Helmen Precision Instruments Co., Ltd., Suzhou, Jiangsu (CN)

(72) Inventors: Kai Jiang, Jiangsu (CN); Yawei Tang, Jiangsu (CN); Ping Wang, Jiangsu (CN)

(73) Assignee: Suzhou Helmen Precision Instruments Co., Ltd., Suzhou (CN)

( * ) Notice: Subject to any disclaimer, the term of this patent is extended or adjusted under 35 U.S.C. 154(b) by 247 days.

(21) Appl. No.: 14/760,685

(22) PCT Filed: Jul. 23, 2014

(86) PCT No.: PCT/CN2014/082832
§ 371 (c)(1),
(2) Date: Jul. 13, 2015

(87) PCT Pub. No.: WO2016/011622
PCT Pub. Date: Jan. 28, 2016

(65) Prior Publication Data
US 2016/0245750 A1 Aug. 25, 2016

(51) Int. Cl.
*G01J 1/58* (2006.01)
*G01N 21/64* (2006.01)

(52) U.S. Cl.
CPC ..... *G01N 21/6408* (2013.01); *G01N 21/6428* (2013.01); *G01N 2021/6413* (2013.01);
(Continued)

(58) Field of Classification Search
CPC .......... G01N 21/6408; G01N 21/6428; G01N 2121/6413; G01N 2121/6439; G01N 2202/061; G01N 2202/12
(Continued)

(56) References Cited

FOREIGN PATENT DOCUMENTS

| CN | 102033048 A | 4/2011 |
| CN | 102735658 | * 10/2012 |

OTHER PUBLICATIONS

English Translation of CN 102735658.*
(Continued)

*Primary Examiner* — David Porta
*Assistant Examiner* — Abra Fein
(74) *Attorney, Agent, or Firm* — Fish & Richardson P.C.

(57) ABSTRACT

The present invention relates to a method for detecting time-resolved fluorescence based on a principle of phase balanced frequency multiplication modulation. A stimulating light source modulated by using a baseband signal acts on a to-be-measured target to trigger fluorescence, so that the fluorescence intensifies and decays periodically; then, a frequency-doubled square signal is used to control a sampling period and divide an ascending period of the fluorescence into two and a decay period of the fluorescence into two; after independent sampling is performed separately, sampling differences of the two parts are separately calculated and then added to obtain an intensity representative value of a fluorescence signal and to obtain a concentration value of the to-be-measured target. The method in the present invention can not only likewise cancel fluorescence interference of a substrate in a sample, but also can cancel ambient bias light, power-frequency interference of a spatial electromagnetic wave or other signals, and therefore improves signal intensity in fluorescence measurement on the detection sample, has an advantage that cannot be
(Continued)

A

B accomplished in a conventional time-resolved fluorescence method, and can be applied in fluorescence intensity detection of a target in fields such as biology, chemistry, and medicine.

7 Claims, 2 Drawing Sheets

(52) U.S. Cl.
CPC ............... *G01N 2021/6439* (2013.01); *G01N 2201/061* (2013.01); *G01N 2201/12* (2013.01)

(58) Field of Classification Search
USPC ...................................................... 250/459.1
See application file for complete search history.

(56) References Cited

OTHER PUBLICATIONS

Zhou, J., et al., "A High Accuracy ATP System Using Modulation Method to Erase effects of Dark Current and Background Light," Application of Electronic Technique, 2007, No. 12, 115-118 and 120 (with English Abstract).

\* cited by examiner

METHOD FOR DETECTING TIME-RESOLVED FLUORESCENCE BASED ON PRINCIPLE OF PHASE BALANCED FREQUENCY MULTIPLICATION MODULATION

TECHNICAL FIELD

The present invention relates to the technical field of testing or analyzing material by testing chemical or physical properties of the material, and in particular, to a method for detecting time-resolved fluorescence based on a principle of phase balanced frequency multiplication modulation, where the method can cancel fluorescence interference of a substrate in a sample, cancel ambient bias light, cancel power-frequency interference of a spatial electromagnetic wave or cancel other signals to improve signal intensity in fluorescence measurement on the detection sample and improve precision of the fluorescence detection.

BACKGROUND

Currently, in most test strips for immunochromatography rapid detection, colloidal gold or a fluorescent pigment is used as a marker. In recent years, a breakthrough has been made in technologies in the immunofluorescence detection field. A time-resolved fluorescence (Time-resolved fluorescence, TRF) immunochromatography technology is developed. This technology has features such as high sensitivity, strong specificity, long fluorescent lifetime, good stability, and no radioactive contamination, and can be widely applied in field quantitative detection, and is an important future development trend for an instant detection technology.

A specific operation process of the time-resolved fluorescence immunochromatography technology is: performing fluorescent pigment dyeing on a testing line (T) and a quality control line (C) on a test strip; placing the test strip into a detection sample, and when the detection sample contains a detection target that can be combined with the fluorescent pigment, performing fluorescent pigment dyeing on a measurement target of the sample; and then, stimulating, by irradiating the sample using stimulating light, the fluorescent pigment to emit fluorescence, and analyzing a final fluorescence intensity value to obtain type, concentration, and other information about the measurement target. This technology requires performing correct analysis on the measurement target according to fluorescence information in a short period of time.

However, in the process of stimulating fluorescence by irradiating the sample using stimulating light, in addition to the fluorescence emitted from the measurement target, that is, fluorescence about which information of a fluorescent pigment is marked on the sample, there are further two categories of interference fluorescence, where the interference fluorescence includes ambient background fluorescence and impurity-stimulated fluorescence. The so-called ambient background fluorescence includes auto-fluorescence of base solution of the sample or the test strip itself, reflected fluorescence that has a relatively wide waveband, leaked light of a detection system and electromagnetic interference, and so on; and the impurity-stimulated fluorescence is mainly a matter that includes a non-measurement target and is in the sample, where this type of matter may also be stimulated by stimulating light to emit fluorescence, only that a process of stimulating and quenching this type of fluorescence is different from a process of stimulating and quenching the measurement target. When a waveband of the foregoing interference fluorescence overlaps a waveband of fluorescence emitted by the fluorescent pigment, if intensity of fluorescence emitted by the interference fluorescence is extremely weak as compared with intensity of fluorescence emitted by the fluorescent pigment, concentration information about the target can be measured by using a traditional time-resolved fluorescence detection method. However, when the fluorescence emitted by the fluorescent pigment is not intense enough, a result of measurement analysis will be badly affected.

In the traditional time-resolved fluorescence detection method, in a process in which fluorescence emission stimulated by the stimulating light by irradiating the sample decays, detection is not performed on the fluorescence when the fluorescence emission is at a maximum value, but the fluorescence detection is delayed for a period of about 200 µs to wait for the impurity-stimulated fluorescence to quench and then starts. In this way, an impact of the foregoing second type of interference fluorescence is canceled and intensity of the fluorescence emitted by the dyed fluorescent pigment is obtained, and relatively accurate information about the measurement target is acquired. In this method, although an impact of that an interfering substance stimulates fluorescence can be canceled, because of an uncertainty of the interfering substance, control over the delay of fluorescence detection is also uncertain. Therefore, it cannot be ensured that fluorescence stimulated by all interfering substances is completely canceled, and the foregoing method cannot be used to cancel interference of the first type of interference fluorescence, the ambient bias light, such as background auto-fluorescence, leaked light of a detection system, or electromagnetic interference.

SUMMARY

The present invention provides an optimized method for detecting time-resolved fluorescence based on a principle of phase balanced frequency multiplication modulation, so as to solve a technical problem that: in the prior art, in a process of stimulating fluorescence by using stimulating light for irradiation, in addition to fluorescence emitted from a measurement target, that is, fluorescence about which information of a fluorescent pigment is marked on a sample, there are further two categories of interference fluorescence, ambient background fluorescence and impurity-stimulated fluorescence; as a result, in a traditional time-resolved fluorescence detection method, in a process in which fluorescence emission stimulated by the stimulating light by irradiating the sample decays, after fluorescence emission reaches a maximum period of time, it is delayed for a period of about 200 µs, and impurity-stimulated fluorescence is waited for quenching, and then, fluorescence detection is performed. In this way, an impact of the foregoing second type of interference fluorescence is canceled and intensity of the fluorescence emitted by a dyed fluorescent pigment is obtained, and relatively accurate information about the measurement target is acquired; however, because of an uncertainty of an interfering substance, control over the delay of fluorescence detection is also uncertain, and therefore, it cannot be ensured that fluorescence stimulated by all interfering substances is completely canceled, and interference of the first type of interference fluorescence, the ambient bias light, cannot be canceled, such as background auto-fluorescence, leaked light of a detection system, or electromagnetic interference.

A technical solution used in the present invention is a method for detecting time-resolved fluorescence based on a principle of phase balanced frequency multiplication modulation, where the method includes the following steps:

step 1.1: generate a regular wave signal in a frequency X as a baseband signal by using a baseband signal generator, where the regular wave signal in the frequency X is used to modulate a stimulating light source, the light source emits stimulating light, and the stimulating light acts on a to-be-measured target to trigger fluorescence;

step 1.2: control a photoelectric sensor to perform, by using N times the frequency X, sampling on the triggered fluorescence, so as to obtain a fluorescence intensity signal $A_i$ at each moment in a sampling period, where i>0 and 30≤N≤80;

step 1.3: perform signal filtering and AD conversion on the fluorescence intensity signal $A_i$ at each moment in the sampling period to obtain a fluorescence intensity digital signal $D_i$ at each moment corresponding to the fluorescence intensity signal $A_i$ at each moment, where i>0;

step 1.4: plot the fluorescence intensity digital signal $D_i$ at each moment according to sampling time to obtain a spectral curve, where the spectral curve includes a fluorescence emission period S and a fluorescence decay period R;

step 1.5: perform frequency multiplication modulation on the baseband signal in the frequency X to produce a frequency-multiplied signal in a frequency X', where X'=2X; divide the fluorescence emission period S into a fluorescence emission period $S_1$ and a fluorescence emission period $S_2$ that have an equal duration and divides the fluorescence decay period R into a fluorescence decay period $R_1$ and a fluorescence decay period $R_2$ that have an equal duration;

step 1.6: perform integral operation on the fluorescence emission periods $S_1$ and $S_2$ and the fluorescence decay periods $R_1$ and $R_2$ on the spectral curve to obtain an integral area of the fluorescence emission period $S_1$ and mark the integral area as $\Phi_1$, obtain an integral area of the fluorescence emission period $S_2$ and mark the integral area as $\Phi_2$, an integral area of the fluorescence decay period $R_1$ and mark the integral area as $\Phi_3$, and an integral area of the fluorescence decay period $R_2$ and mark the integral area as $\Phi_4$, where $\Phi_2 > \Phi_1 > 0$ and $\Phi_3 > \Phi_4 > 0$;

step 1.7: subtract the integral area $\Phi_1$ of the fluorescence emission period $S_1$ from the integral area $\Phi_2$ of the fluorescence emission period $S_2$ to obtain $S'=\Phi_2-\Phi_1$, where S' is marked as a fluorescence intensity value of a fluorescence emission period; subtract the integral area $\Phi_4$ of the fluorescence decay period $R_2$ from the integral area $\Phi_3$ of the fluorescence decay period $R_1$ to obtain $R'=\Phi_3-\Phi_4$, where R' is marked as a fluorescence intensity value of a fluorescence decay period; add the fluorescence intensity value S' of the fluorescence emission period to the fluorescence intensity value R' of the fluorescence decay period to obtain $\Delta\Phi=\Phi_2-\Phi_1+\Phi_3-\Phi_4$ and mark the $\Delta\Phi$ as a total fluorescence intensity value of fluorescence pigment emission, where S'>0 and R'>0; and step 1.8: obtain a concentration value of the to-be-measured target by using a calibration method by using the total fluorescence intensity value $\Delta\Phi$ of the fluorescence pigment emission to represent a fluorescence signal measurement value of the to-be-measured target.

Preferably, in step 1.1, the regular wave signal in the frequency X generated by using the baseband signal generator is a square signal.

Preferably, in step 1.1, the stimulating light source is modulated by the baseband square signal.

Preferably, in step 1.2, N=50.

Preferably, in step 1.2, the photoelectric sensor is configured as a photodiode.

Preferably, in step 1.3, the signal filtering and AD conversion include the following steps:

step 2.1: perform signal amplification on the fluorescence intensity signal $A_i$ at each moment that is obtained by performing sampling using N times the sampling frequency X, so as to obtain an amplified fluorescence intensity signal $A_i'$;

step 2.2: perform filtering on the amplified fluorescence intensity signal $A_i'$ by using a high-pass filtering module, so as to filter out low-frequency noises and power-frequency interference; and step 2.3: perform conversion on the filtered amplified fluorescence intensity signal $A_i'$ by using an analog-to-digital conversion module, so as to obtain the fluorescence intensity digital signal $D_i$ at each moment in the sampling period corresponding to the fluorescence intensity signal $A_i$ at each moment in the sampling period.

Preferably, in step 1.3, the filtering is median filtering.

The present invention provides an optimized method for detecting time-resolved fluorescence based on a principle of phase balanced frequency multiplication modulation. A stimulating light source modulated by using a baseband signal acts on a to-be-measured target to trigger fluorescence, so that the fluorescence intensifies and decays periodically; then, a frequency-doubled square signal is used to control a sampling period and divide an ascending period of the fluorescence into two and a decay period of the fluorescence into two; after independent sampling is performed separately, sampling differences of the two parts are separately calculated and then added to obtain an intensity representative value of a fluorescence signal and to obtain a concentration value of the to-be-measured target. The method in the present invention can not only likewise cancel fluorescence interference of a substrate in a sample, but also can cancel ambient bias light, power-frequency interference of a spatial electromagnetic wave or other signals, and therefore improves signal intensity in fluorescence measurement on the detection sample, has an advantage that cannot be accomplished in a conventional time-resolved fluorescence method, and can be applied in fluorescence intensity detection of a target in fields such as biology, chemistry, and medicine.

DESCRIPTION OF EMBODIMENTS

Figure 1:
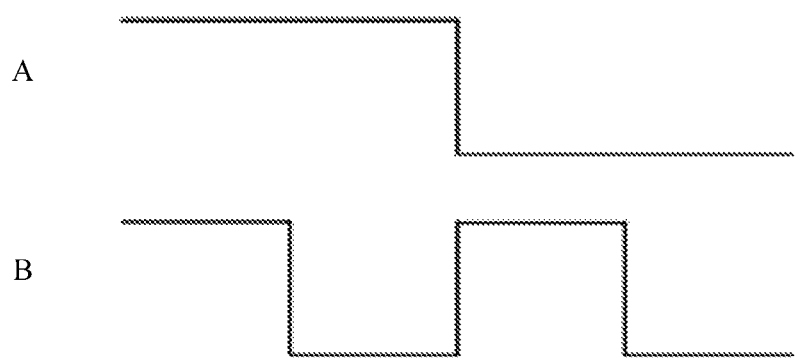
FIG. 1 is a schematic diagram of a baseband signal and a frequency-multiplied signal in the present invention, where A is the baseband signal and B is the frequency-multiplied signal.

The following further describes the present invention in detail with reference to embodiments, but are not intended to limit the protection scope of the present invention.

The present invention relates to a method for detecting time-resolved fluorescence based on a principle of phase balanced frequency multiplication modulation, where the method includes the following steps:

step 1.1: generate a regular wave signal in a frequency X as a baseband signal by using a baseband signal generator, where the regular wave signal in the frequency X is used to modulate a stimulating light source, the light source emits stimulating light, and the stimulating light acts on a to-be-measured target to trigger fluorescence;

step 1.2: control a photoelectric sensor to perform, by using N times the frequency X, sampling on the triggered fluorescence, so as to obtain a fluorescence intensity signal $A_i$ at each moment in a sampling period, where i>0 and 30≤N≤80;

step 1.3: perform signal filtering and AD conversion on the fluorescence intensity signal $A_i$ at each moment in the sampling period to obtain a fluorescence intensity digital signal $D_i$ at each moment corresponding to the fluorescence intensity signal $A_i$ at each moment, where i>0;

step 1.4: plot the fluorescence intensity digital signal $D_i$ at each moment according to sampling time to obtain a spectral curve, where the spectral curve includes a fluorescence emission period S and a fluorescence decay period R;

step 1.5: perform frequency multiplication modulation on the baseband signal in the frequency X to produce a frequency-multiplied signal in a frequency X', where X'=2X; divide the fluorescence emission period S into a fluorescence emission period $S_1$ and a fluorescence emission period $S_2$ that have an equal duration and divides the fluorescence decay period R into a fluorescence decay period $R_1$ and a fluorescence decay period $R_2$ that have an equal duration;

step 1.6: perform integral operation on the fluorescence emission periods $S_1$ and $S_2$ and the fluorescence decay periods $R_1$ and $R_2$ on the spectral curve to obtain an integral area of the fluorescence emission period $S_1$ and mark the integral area as $\Phi_1$, obtain an integral area of the fluorescence emission period $S_2$ and mark the integral area as $\Phi_2$, an integral area of the fluorescence decay period $R_1$ and mark the integral area as $\Phi_3$, and an integral area of the fluorescence decay period $R_2$ and mark the integral area as $\Phi_4$, where $\Phi_2>\Phi_1>0$ and $\Phi_3>\Phi_4>0$;

step 1.7: subtract the integral area $\Phi_1$ of the fluorescence emission period $S_1$ from the integral area $\Phi_2$ of the fluorescence emission period $S_2$ to obtain $S'=\Phi_2-\Phi_1$, where S' is marked as a fluorescence intensity value of a fluorescence emission period; subtract the integral area $\Phi_4$ of the fluorescence decay period $R_2$ from the integral area $\Phi_3$ of the fluorescence decay period $R_1$ to obtain $R'=\Phi_3-\Phi_4$, where R' is marked as a fluorescence intensity value of a fluorescence decay period: add the fluorescence intensity value S' of the fluorescence emission period to the fluorescence intensity value R' of the fluorescence decay period to obtain $\Delta\Phi=\Phi_2-\Phi_1+\Phi_3-\Phi_4$ and mark the $\Delta\Phi$ as a total fluorescence intensity value of fluorescence pigment emission, where S'>0 and R'>0; and step 1.8: obtain a concentration value of the to-be-measured target by using a calibration method by using the total fluorescence intensity value $\Delta\Phi$ of the fluorescence pigment emission to represent a fluorescence signal measurement value of the to-be-measured target.

In the method provided in the present invention, a measurement target emits fluorescence by means of irradiation by stimulating light and an obtained fluorescence signal is processed, and therefore, a fluorescence intensity value can be rapidly and easily calculated and then a concentration value of the target is obtained by using a calibration method.

Figure 2:
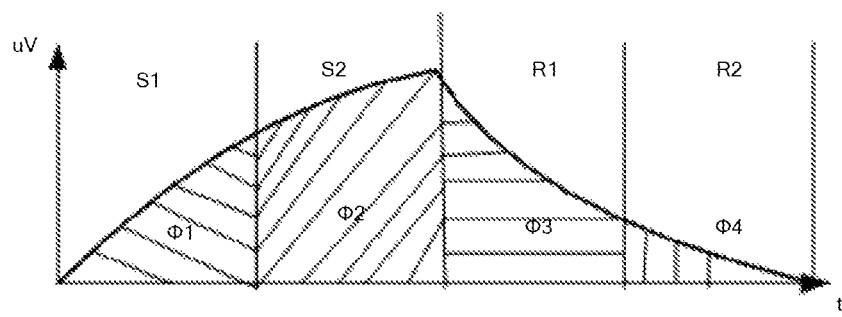
FIG. 2 is a schematic diagram of performing integral operation on fluorescence emission periods $S_1$ and $S_2$ and fluorescence decay periods $R_1$ and $R_2$ on the spectral curve in step 1.6 in the present invention.

In the present invention, in step 1.1, a baseband signal A in a frequency X shown in FIG. 1 is used to complete work of controlling a stimulating light source and triggering a to-be-measured target to emit fluorescence. In step 1.2, a sampling action is controlled by using N times the frequency X and to perform sampling on to-be-triggered fluorescence. An advantage of step 1.2 lies in that the frequency is relatively high, and therefore, a fluorescence intensity spectral curve of an undistorted fluorescence emission and decay process can be obtained. Step 1.3 is a digital-to-analog conversion process and signal demodulation and filtering on a fluorescence intensity signal $A_i$ at each moment in a sampling period are completed at the same time, ensuring elimination of a jitter that occurs on the fluorescence due to a cause such as a surface is rough and there is a background interference matter. In step 1.4, when the fluorescence intensity signal $A_i$ at each moment is converted into a fluorescence intensity digital signal digit $D_i$ at each moment, which actually is a voltage value at each moment, that is, symbolizes light intensity at each moment, and can be used to make the spectral curve that is based on a fluorescence detection time period and fluorescence intensity value and perform integration according to the spectral curve to obtain a spectral integral curve. In this case, the curve has significant ascending branch and descending branch, the ascending branch of the spectral curve is a fluorescence emission period S and the descending branch of the spectral curve is a fluorescence decay period R. In step 1.5, a frequency-multiplied signal B in a frequency 2X shown in FIG. 1 is used to perform frequency multiplication modulation, the fluorescence emission period S is divided into two parts that have an equal duration and the fluorescence decay period R is divided into two parts that have an equal duration. In step 1.6, integral operation is performed, in the spectral curve, on the two parts of the fluorescence emission period S that have the equal duration and the two parts of the fluorescence decay period R that have the equal duration, so as to obtain an integral area of the two parts of the fluorescence emission period S and an integral area of the two parts of the fluorescence decay period R, where an integral area of a fluorescence emission period $S_1$ is marked as $\Phi_1$, an integral area of a fluorescence emission period $S_2$ is marked as $\Phi2$, an integral area of a fluorescence decay period $R_1$ is marked as $\Phi_3$, and an integral area of a fluorescence decay period $R_2$ is marked as $\Phi_4$, as shown in FIG. 2. In step 1.7, subtraction is performed on the integral areas of the two parts of the fluorescence emission period S to obtain a fluorescence intensity value $\Phi_2-\Phi_1$ of a fluorescence emission period, and subtraction is performed on the integral areas of the two parts of the fluorescence decay period R to obtain a fluorescence intensity value $\Phi_3-\Phi_4$ of a fluorescence decay period. In this case, fluorescence interference of a substrate in a sample that is also in the fluorescence emission period or the fluorescence decay period has been canceled in the fluorescence intensity value of the fluorescence emission period and the fluorescence intensity value of the fluorescence decay period, interference of ambient bias light, power-frequency interference of a spatial electromagnetic wave or other signals that are also in the fluorescence emission period or the fluorescence decay period is also canceled. In addition, because the used integral areas of the fluorescence emission period and fluorescence decay period have an equal duration each, only one time of subtraction is required each to obtain an actual fluorescence intensity value in the fluorescence emission period and an actual fluorescence intensity value in the fluorescence decay period. Finally, the actual fluorescence intensity value in the fluorescence emission period and the actual fluorescence intensity value in the fluorescence decay period are added to obtain a total fluorescence intensity value $\Delta\Phi=\Phi_2-\Phi_1+\Phi_3-\Phi_4$ of fluorescence pigment emission. This is simple and easy to operate. In step 1.8, a concentration value of the to-be-measured target is obtained by using a calibration method on the total fluorescence intensity value $\Delta\Phi$ to of the fluorescence pigment emission, so that detection of concentration of the to-be-measured target is complete.

The method used in the present invention can not only cancel fluorescence interference of a substrate in a to-be-measured target, but also can cancel ambient bias light, power-frequency interference of a spatial electromagnetic wave or other signals, and therefore improves signal intensity in fluorescence measurement on the to-be-measured target, is more secure and reliable, has strong feasibility and strong operability, and has an advantage that cannot be accomplished in a conventional time-resolved fluorescence method.

In the present invention, a stimulating light source is configured to be enabled and disabled according to a frequency X, so that fluorescence is triggered to intensify and decay periodically, thereby achieving an objective of controlling an emission period and a decay period of fluorescence of to-be-measured target.

In the present invention, stimulating light may be a common light source such as a light emitting diode, or may also be configured as a laser.

In the present invention, a frequency X of a stimulating light source is determined according to a stimulating wavelength of a fluorescence-stimulated matter. For different to-be-measured targets, stimulating wavelengths of the different to-be-measured targets are different.

In the present invention, the calibration method in step 1.8 includes the following steps:

step 3.1: perform fluorescence stimulation on a sample with a standard concentration;

step 3.2: measure a light intensity value corresponding to the sample with the standard concentration;

step 3.3: perform conversion on the light intensity value by means of piecewise linear interpolation, so as to obtain concentration values of the target corresponding to different fluorescence intensity values; and step 3.4: perform corresponding query to obtain a fluorescence signal measurement value of a to-be-measured target corresponding to a total fluorescence intensity value $\Delta\Phi$ of fluorescence pigment emission.

In the present invention, a calibration method is used to determine a fluorescence signal measurement value of a to-be-measured target corresponding to a total fluorescence intensity value $\Delta\Phi$ of fluorescence pigment emission. One reason is that the calibration method is to detect, by using a standard metering manner, whether precision of the detected fluorescence signal measurement value meets a standard, and the calibration method is applicable to high-precision measurement. Another reason is that the calibration method is also applicable to alignment and ensures precision of the fluorescence signal measurement value.

In step 1.1, the regular wave signal in the frequency X generated by using the baseband signal generator is a square signal.

In the present invention, a regular wave signal in a frequency X generated by using a baseband signal generator is configured as a square signal. Because an ideal square wave changes instantaneously between two large and small values, by using a square wave in the present invention to function as a baseband signal and using the baseband signal in a subsequent step to produce a frequency-multiplied signal that is also a square signal, entire data processing is more simple and is capable of more intuitively displaying the spectral curve related in the present invention.

In step 1.1, the stimulating light source is modulated by using the baseband square signal.

In the present invention, the baseband square signal is used to modulate a stimulating light source. This ensures stability of the stimulating light source and in a process in which the stimulating light source is stimulated, enables the stimulating light source to act stably and uniformly on a to-be-measured target to trigger fluorescence.

In the present invention, different colors of stimulating light are used in stimulating light sources with different wavelengths.

In the present invention, because the stimulating light source is modulated by using the baseband square signal in step 1.1, an optical detection module is generally configured as a dual-light source reflective optical detection module that relates to design of a light path of a bi-conjugate structure. In an actual operating process, an LED with high stability is generally used to stimulate a light source and a photoelectric sensor is used to detect fluorescence light intensity in a current scanning position and transmit information to a control circuit for analysis processing and to finally obtain concentration data of a to-be-measured target.

In the present invention, an LED is generally used to complete work of a stimulating light source, because the LED has advantages such as narrow spectral bandwidth, low temperature coefficient, and small-angle scattering.

In step 1.2, N=50.

In the present invention, N is set to 50 in the controlling a photoelectric sensor to perform, by using N times the frequency X, sampling on the triggered fluorescence in step 1.2. Generally, in a sampling frequency with N being 50, signals at each point can be better obtained by means of sampling and a spectral curve is not distorted due to excessively intensive sampling.

In step 1.2, the photoelectric sensor is configured as a photodiode.

In the present invention, a photoelectric sensor is a frequently used sensor in which a photodiode component is used as a detection component. The photoelectric sensor can convert an optical signal into an electrical signal by using the photodiode component in a change of the optical signal. In the present invention, any photoelectric sensor that can convert an optical signal into an electrical signal is applicable to step 1.2. Generally, using a photodiode is sufficient to meet requirements of the invention.

In step 1.3, the signal filtering and AD conversion include the following steps:

step 2.1: perform signal amplification on the fluorescence intensity signal $A_i$ at each moment that is obtained by performing sampling using N times the sampling frequency X, so as to obtain an amplified fluorescence intensity signal $A_i'$;

step 2.2: perform filtering on the amplified fluorescence intensity signal $A_i'$ by using a high-pass filtering module, so as to filter out low-frequency noises and power-frequency interference; and step 2.3: perform conversion on the filtered amplified fluorescence intensity signal $A_i'$ by using an analog-to-digital conversion module, so as to obtain the fluorescence intensity digital signal $D_i$ at each moment in the sampling period corresponding to the fluorescence intensity signal $A_i$ at each moment in the sampling period.

In the present invention, in signal demodulation, an optical signal of a light source needs to be modulated to a frequency X and converted into an effective voltage signal. Then, a fluorescence intensity signal $A_i$ at each moment in a sampling period is amplified and low-frequency noises and power-frequency interference are filtered out by using a high-pass filtering module. After the noises and the interference are filtered out, simultaneous demodulation is performed by using a baseband signal in the frequency X and a frequency-multiplied signal in a frequency X'. Finally, a demodulation result is sent to an analog-to-digital conversion module to obtain a digital signal $D_i$ with corresponding fluorescence light intensity.

In the present invention, an analog-to-digital conversion module can be accomplished by using a high-precision and low-noise 24-bit $\Sigma$-$\Delta$ type AD conversion chip.

In the present invention, because there is still an interference signal in a sampling result obtained by means of scanning by a photoelectric sensor, in step 1.3, signal filtering and AD conversion are performed on a fluorescence intensity signal $A_i$ at each moment in a sampling period to obtain a fluorescence intensity digital signal $D_i$ at each moment corresponding to the fluorescence intensity signal $A_i$ at each moment. Generally, a control circuit is configured to meet requirements for the photoelectric sensor to feed back sampled information obtained by means of scanning to a CPU, and an optical signal of a light source is modulated, by using a photoelectric signal IV conversion module, to a frequency and converted into an effective voltage signal. Then, low-frequency noises and power-frequency interference are filtered out by using a signal amplification filtering module and a fluorescence intensity signal is converted from an analog signal into a digital signal by using an AD conversion module, so that fluorescence intensity of the digital signal obtained after the conversion is obtained and subsequent analysis and calculation is performed to finally obtain an actual concentration value of a to-be-measured target.

In step 1.3, the filtering is median filtering.

In the present invention, median filtering is a nonlinear signal processing technology based on the order statistical theory and can effectively suppress noises. A basic principle of the median filtering is to replace a value at a point in a digital image or a digital sequence with a median of values of points in a neighborhood of the point, so that surrounding resolution values are close to real values, thereby canceling isolated noise points. A merit of the median filtering lies in that edge information can be protected. The median filtering is a typical noise smoothing method.

In the present invention, a method for detecting time-resolved fluorescence based on a principle of phase balanced frequency multiplication modulation can be accomplished by configuring a related device. The device can be configured by a person skilled in the art based on the method in the present invention. Generally, an optical detection agency and a control circuit are configured inside a housing of the device. A test stripe of a to-be-measured target is configured to be inserted into a test stripe slot of the housing. The control circuit controls an optical detection module to perform detection and scanning and sampling on fluorescence intensity of the to-be-measured target on the test stripe. Emission light intensity of a fluorescence marker in a control line (C) and a measurement line (T) on a fluorescence chromatography test stripe is collected and a spectral sampling information curve is marked and displayed. The control circuit performs analysis on the fluorescence intensity to obtain concentration of the target.

In the present invention, a time-resolved fluorescence technology based chromatography test stripe can be selected to add detection samples of different concentration. After the test stripe is dry completely, detection is performed for multiple times on a signal on a control line (C) and a measurement line (T) of the test stripe and stability of T/C values of the test stripe is observed. Because of fluorescence bleaching effects, absolute light intensity on both line C and line T decays, but the T/C value retains relatively stable, and an indicator of 0.5% detection sensitivity can be achieved.

The present invention solves a problem in the prior art that: in a process of stimulating fluorescence by using stimulating light for irradiation, in addition to fluorescence emitted from a measurement target, that is, fluorescence about which information of a fluorescent pigment is marked on a sample, there are further two categories of interference fluorescence, ambient background fluorescence and impurity-stimulated fluorescence; as a result, in a traditional time-resolved fluorescence detection method, in a process in which fluorescence emission stimulated by the stimulating light by irradiating the sample decays, after fluorescence emission reaches a maximum period of time, it is delayed for a period of about 200 μs, and impurity-stimulated fluorescence is waited for quenching, and then, fluorescence detection is performed. In this way, an impact of the foregoing second type of interference fluorescence is canceled and intensity of the fluorescence emitted by a dyed fluorescent pigment is obtained, and relatively accurate information about the measurement target is acquired; however, because of an uncertainty of an interfering substance, control over the delay of fluorescence detection is also uncertain, and therefore, it cannot be ensured that fluorescence stimulated by all interfering substances is completely canceled, and interference of the first type of interference fluorescence, the ambient bias light, cannot be canceled, such as background auto-fluorescence, leaked light of a detection system, or electromagnetic interference. A stimulating light source modulated by using a baseband signal acts on a to-be-measured target to trigger fluorescence, so that the fluorescence intensifies and decays periodically; then, a frequency-doubled square signal is used to control a sampling period and divide an ascending period of the fluorescence into two and a decay period of the fluorescence into two; after independent sampling is performed separately, sampling differences of the two parts are separately calculated and then added to obtain an intensity representative value of a fluorescence signal and to obtain a concentration value of the to-be-measured target. The method in the present invention can not only likewise cancel fluorescence interference of a substrate in a sample, but also can cancel ambient bias light, power-frequency interference of a spatial electromagnetic wave or other signals, and therefore improves signal intensity in fluorescence measurement on the detection sample, has an advantage that cannot be accomplished in a conventional time-resolved fluorescence method, and can be applied in fluorescence intensity detection of a target in fields such as biology, chemistry, and medicine.

What is claimed is:

1. A method for detecting time-resolved fluorescence based on a principle of phase balanced frequency multiplication modulation, wherein the method comprises the following steps:

step 1-1: generate a regular wave signal in a frequency X as a baseband signal by using a baseband signal generator, wherein the regular wave signal in the frequency X is used to modulate a stimulating light source, the light source emits stimulating light, and the stimulating light acts on a to-be-measured target to trigger fluorescence;

step 1-2: control a photoelectric sensor to perform, by using N times the frequency X, sampling on the triggered fluorescence, so as to obtain a fluorescence intensity signal $A_i$ at each moment in a sampling period, wherein i>0 and 30≤N≤80;

step 1-3: perform signal filtering and AD conversion on the fluorescence intensity signal $A_i$ at each moment in the sampling period to obtain a fluorescence intensity digital signal $D_i$ at each moment corresponding to the fluorescence intensity signal $A_i$ at each moment, wherein i>0;

step 1-4: plot the fluorescence intensity digital signal Di at each moment according to sampling time to obtain a spectral curve, wherein the spectral curve comprises a fluorescence emission period S and a fluorescence decay period R;

step 1-5: perform frequency multiplication modulation on the baseband signal in the frequency X to produce a frequency-multiplied signal in a frequency X', wherein X'=2X; divide the fluorescence emission period S into a fluorescence emission period $S_1$ and a fluorescence emission period $S_2$ that have an equal duration and divides the fluorescence decay period R into a fluorescence decay period $R_1$ and a fluorescence decay period $R_2$ that have an equal duration;

step 1-6: perform integral operation on the fluorescence emission periods $S_1$ and $S_2$ and the fluorescence decay periods $R_1$ and $R_2$ on the spectral curve to obtain an integral area of the fluorescence emission period $S_1$ and mark the integral area as $\Phi_1$, obtain an integral area of the fluorescence emission period $S_2$ and mark the integral area as $\Phi_2$, an integral area of the fluorescence decay period $R_1$ and mark the integral area as $\Phi_3$, and an integral area of the fluorescence decay period $R_2$ and mark the integral area as $\Phi_4$, wherein $\Phi_2 > \Phi_1 > 0$ and $\Phi_3 > \Phi_4 > 0$;

step 1-7: subtract the integral area $\Phi_1$ of the fluorescence emission period $S_1$ from the integral area $\Phi_2$ of the fluorescence emission period $S_2$ to obtain $S' = \Phi_2 - \Phi_1$, wherein S' is marked as a fluorescence intensity value of a fluorescence emission period; subtract the integral area $\Phi_4$ of the fluorescence decay period $R_2$ from the integral area $\Phi_3$ of the fluorescence decay period $R_1$ to obtain $R = \Phi_3 - \Phi_4$, wherein R' is marked as a fluorescence intensity value of a fluorescence decay period; add the fluorescence intensity value S' of the fluorescence emission period to the fluorescence intensity value R' of the fluorescence decay period to obtain $\Delta\Phi = \Phi_2 - \Phi_1 + \Phi_3 - \Phi_4$ and mark the $\Delta\Phi$ as a total fluorescence intensity value of fluorescence pigment emission, wherein S'>0 and R'>0; and step 1-8: obtain a concentration value of the to-be-measured target by using a calibration method by using the total fluorescence intensity value $\Delta\Phi$ of the fluorescence pigment emission to represent a fluorescence signal measurement value of the to-be-measured target.

2. The method for detecting time-resolved fluorescence based on a principle of phase balanced frequency multiplication modulation according to claim 1, wherein: in step 1-1, the regular wave signal in the frequency X generated by using the baseband signal generator is a square signal.

3. The method for detecting time-resolved fluorescence based on a principle of phase balanced frequency multiplication modulation according to claim 2, wherein: in step 1-1, the stimulating light source is modulated by using the square signal.

4. The method for detecting time-resolved fluorescence based on a principle of phase balanced frequency multiplication modulation according to claim 1, wherein: in step 1-2, N=50.

5. The method for detecting time-resolved fluorescence based on a principle of phase balanced frequency multiplication modulation according to claim 1, wherein: in step 1-2, the photoelectric sensor is configured as a photodiode.

6. The method for detecting time-resolved fluorescence based on a principle of phase balanced frequency multiplication modulation according to claim 1, wherein: in step 1-3, the signal filtering and AD conversion comprise the following steps:

step 2-1: perform signal amplification on the fluorescence intensity signal $A_i$ at each moment that is obtained by performing sampling using N times the sampling frequency X, so as to obtain an amplified fluorescence intensity signal $A_i'$;

step 2-2: perform filtering on the amplified fluorescence intensity signal $A_i'$ by using a high-pass filtering module, so as to filter out low-frequency noises and power-frequency interference; and step 2-3: perform conversion on the filtered amplified fluorescence intensity signal $A_i'$ by using an analog-to-digital conversion module, so as to obtain the fluorescence intensity digital signal $D_i$ at each moment in the sampling period corresponding to the fluorescence intensity signal $A_i$ at each moment in the sampling period.

7. The method for detecting time-resolved fluorescence based on a principle of phase balanced frequency multiplication modulation according to claim 1, wherein: in step 1-3, the filtering is median filtering.

* * * * *

UNITED STATES PATENT AND TRADEMARK OFFICE
CERTIFICATE OF CORRECTION

PATENT NO.         : 9,869,638 B2
APPLICATION NO.    : 14/760685
DATED              : January 16, 2018
INVENTOR(S)        : Kai Jiang, Yawei Tang and Ping Wang Page 1 of 1

It is certified that error appears in the above-identified patent and that said Letters Patent is hereby corrected as shown below:

In the Claims

Column 11, Line 39, Claim 1, delete "$R=\Phi_3-\Phi_4$," and insert --$R'=\Phi_3-\Phi_4$,--.

Signed and Sealed this
Tenth Day of April, 2018

Andrei Iancu
*Director of the United States Patent and Trademark Office*